United States Patent

Stringer et al.

Patent Number: 5,912,274

Date of Patent: *Jun. 15, 1999

[54] ANTIPLAQUE ORAL COMPOSITION AND METHOD

[75] Inventors: Orum D. Stringer, Yardley, Pa.; John C. Brahms, Trenton, N.J.; Malathy Subramanian, Branchburg, N.J.; Ernest E. Kelly, New Brunswick, N.J.

[73] Assignee: Colgate-Palmolive Company, New York, N.Y.

[21] Appl. No.: 08/823,499

[22] Filed: Mar. 25, 1997

Related U.S. Application Data

[63] Continuation-in-part of application No. 08/649,389, May 17, 1996, Pat. No. 5,723,500
[60] Provisional application No. 60/004,196, Sep. 22, 1995.
[51] Int. Cl.$^6$ .......................... A01N 31/08; A61K 31/05; A61K 7/16; A61K 7/18
[52] U.S. Cl. .............. 514/731; 424/49; 424/52; 514/901
[58] Field of Search ................ 424/49, 52; 514/731, 514/901

[56] References Cited

U.S. PATENT DOCUMENTS

| | | | |
|---|---|---|---|
| 3,800,051 | 3/1974 | Barnhart et al. | 424/346 |
| 4,067,997 | 1/1978 | Kabara | 424/312 |
| 4,321,257 | 3/1982 | Sipos | 424/80 |
| 5,188,821 | 2/1993 | Gaffar et al. | 424/52 |
| 5,487,893 | 1/1996 | Vachy | 424/195.1 |

FOREIGN PATENT DOCUMENTS

| | | |
|---|---|---|
| 199751 | 12/1982 | Czechoslovakia . |
| 2128026 | 10/1972 | France . |
| 553142 | 8/1974 | Switzerland . |
| 9210992 | 7/1992 | WIPO . |
| WO 92/10992 | 7/1992 | WIPO . |

OTHER PUBLICATIONS

Chemical Abstracts vol. 93, No. 17, Oct. 27, 1980.
(Abstract No. 162715—Japan Kokai 55 016 802—Ajinomoto).

*Primary Examiner*—José G. Dees
*Assistant Examiner*—Marina Lamm
*Attorney, Agent, or Firm*—Henry S. Goldfine; Robert L. Stone

[57] ABSTRACT

An oral antiplaque composition for treatment of teeth wherein the essential antiplaque agent is a substantially water insoluble noncationic antibacterial phenol containing, relative to the hydroxyl group, an alkyl or cycloalkyl group, preferably tert.-butyl (t-butyl), in the 2-position, and substituents in one or both of the 4- and 5-positions, one or both of which may be alkyl or cycloalkyl, one being preferably t-butyl.

31 Claims, No Drawings

ANTIPLAQUE ORAL COMPOSITION AND METHOD

CROSS-REFERENCES TO RELATED APPLICATIONS

This is a continuation-in-part of application Ser. No. 08/649,389 filed May 17, 1996, now U.S. Pat. No. 5,723,500 issued Mar. 3, 1998, which claims priority of Provisional Application Ser. No. 60/004,196 filed Sep. 22, 1995.

BACKGROUND OF THE INVENTION

1. Field of the Invention

This invention relates to antibacterial antiplaque oral compositions and also to compositions containing a novel essential antiplaque component comprising a substantially water insoluble, noncationic antibacterial alkylated phenol compound more fully described below and to a selected group of such compounds which are considered novel.

2. Description of the Prior Art

Dental plaque is a soft deposit which forms on teeth as opposed to calculus which is a hard calcified deposit on teeth. Unlike calculus, plaque may form on any part of the tooth surface, particularly including at the gingival margin. Hence, beside being unsightly, it is implicated in the occurrence of gingivitis.

Accordingly, it is highly desirable to include antimicrobial (antibacterial) agents in oral compositions to reduce plaque.

The cationic antibacterial materials such as chlorhexidine, benzethonium chloride and cetyl pyridinium chloride have been the subject of greatest investigation as antibacterial antiplaque agents. However, they are generally not effective when used with anionic materials. Noncationic antibacterial materials, on the other hand, can be compatible with anionic components in an oral composition.

However, oral compositions typically are mixtures of numerous components and even such typically neutral materials as humectants can affect performance of such compositions.

Halogenated hydroxydiphenyl ethers such as triclosan have been very effectively employed in oral compositions as antibacterial antiplaque agents. However, it is desirable to be able to provide non-halogenated agents which are highly effective and possibly even more effective than triclosan.

Phenol and alkyl substituted phenols are well known and widely used antimicrobials. Thymol (2-isopropyl-5-methylphenol) is an active antimicrobial agent in commercial mouthrinse formulations, but its anti-microbial activity is considered relatively low and possibly insufficient, its activity for example being only a small fraction of the activity of triclosan. Hitherto, alternatives to triclosan having substantially greater antiplaque activity than thymol or than monoalkyl phenols and optimally comparable to or even greater then the activity of triclosan have not been available.

It is an object of this invention to provide an antiplaque oral composition with substantial antiplaque effectiveness containing noncationic phenolic oral antibacterial antiplaque agents (AA) as alternatives to triclosan. Another object is to provide alkyl phenolic AA's which, except for the single OH group, are entirely hydrocarbon and which have oral antimicrobial activities up to 100 or more times the activity of thymol, for instance up to as much as or exceeding the activity of triclosan. A further object is to provide such AA's which are, or can be expected to be, found in nature, e.g. plant material, etc. Still another object is to provide novel AA's. Other objects and advantages will appear as the description proceeds.

SUMMARY OF THE INVENTION

In accordance with some of its aspects, this invention relates to an oral antiplaque composition comprising an orally acceptable vehicle and an effective antiplaque amount of at least one substantially water insoluble noncationic monohydroxy AA having the following formula:

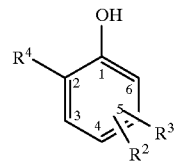

wherein $R^2$ and $R^3$ are interchangeably substituted in the 4 and 5 positions; wherein $R^4$ is defined below, wherein:

(a) when $R^4$ is $C_1$ n-alkyl it is partially or fully substituted with $C_{3-6}$ cycloalkyl, optionally partially or fully substituted with C3–6 cycloalkyls or $C_{1-7}$ side chains alkyls and $R^2$ is (1) a $C_{1-8}$ n-alkyl, optionally partially or fully substituted with C3–6 cycloalkyls or $C_{1-7}$ side chain alkyls or (2) a $C_{3-6}$ cycloalkyls, optionally partially or fully substituted with C1–7 side chain alkyls or $C_{3-6}$ cycloalkyls and $R^3$ is (1) H or (2) a $C_{1-8}$ n-alkyl, optionally partially or fully substituted with C3–6 cycloalkyls or $C_{1-7}$ side chain alkyls or (3) a $C_{3-6}$ cycloalkyl optionally partially or fully substituted with $C_{1-7}$ side chain alkyls or $C_{3-6}$ cycloalkyls;

(b) when $R^4$ is $C_2$ n-alkyl and $R^4$ is ethyl or isopropyl it is optionally partially or fully substituted with $C_{3-6}$ cycloalkyls optionally partially or fully substituted with $C_{1-7}$ side chain alkyls or $C_{3-6}$ cycloalkyls and $R^2$ is (1) a $C_{4-8}$ n-alkyl, optionally partially or fully substituted with $C_{3-6}$ cycloalkyls or $C_{1-7}$ side chain alkyls or (2) a $C_{3-6}$ cycloalkyl, optionally partially or fully substituted with C1–7 side chain alkyls or $C_{3-6}$ cycloalkyls and $R^3$ is (1) H or (2) a $C_{1-8}$ n-alkyl, optionally partially or fully substituted with $C_{3-6}$ cycloalkyl or $C_{1-7}$ side chain alkyls or (3) a $C_{3-6}$ cycloalkyl, optionally partially or fully substituted with $C_{1-7}$ side chain alkyls or $C_{3-6}$ cycloalkyls;

(c) when $R^4$ is $C_2$ n-alkyl and $R^4$ is t-butyl it is optionally partially or fully substituted with $C_{3-6}$ cycloalkyls optionally partially or fully substituted with $C_{1-7}$ side chain alkyls or $C_{3-6}$ cycloalkyls and $R^2$ is (1) a $C_{1-8}$ n-alkyl, optionally partially or fully substituted with $C_{3-6}$ cycloalkyls or $C_{1-7}$ side chain alkyls or (2) a $C_{3-6}$ cycloalkyl, optionally partially or fully substituted with C1–7 side chain alkyls or $C_{3-6}$ cycloalkyls and $R^3$ is (1) H or (2) a $C_{1-8}$ n-alkyl, optionally partially or fully substituted with C3–6 cycloalkyls or $C_{1-7}$ side chain alkyls or (3) $C_{3-6}$ cycloalkyl, optionally partially or fully substituted with $C_{1-7}$ side chain alkyls or $C_{3-6}$ cycloalkyls;

(d) when $R^4$ is $C_{3-8}$ n-alkyl it is optionally partially or fully substituted with $C_{3-6}$ cycloalkyls optionally partially or fully substituted with $C_{1-7}$ side chain alkyls or $C_{3-6}$ cycloalkyls or $C_{1-7}$ side chain alkyls optionally partially or fully substituted with C3–6 cycloalkyls and $R^2$ is (1) a $C_{2-8}$ n-alkyl, optionally partially or fully substituted with $C_{3-6}$ cycloalkyls or $C_{1-7}$ side chain alkyls or (2) a $C_{3-6}$ cycloalkyl; optionally partially or fully substituted with C1–7 side chains or $C_{3-6}$ cycloalkyls and $R^3$ is (1) H or (2) a $C_{2-8}$ n-alkyl, optionally partially or fully substituted with $C_{3-6}$ cycloalkyls or $C_{1-7}$ side chain alkyls or (3) a $C_{3-6}$ cycloalkyl, optionally partially or fully substituted with $C_{1-7}$ side chain alkyls or $C_{3-6}$ cycloalkyls and (e) when $R^4$ is $C_{3-6}$ cycloalkyl it is optionally partially or fully substituted with $C_{1-7}$ side chain alkyls or $C_{3-6}$ cycloalkyls and $R^2$ is (1) a $C_{4-8}$ n-alkyl, optionally partially or fully substituted with $C_{3-6}$ cycloalkyls or $C_{1-7}$ side chain alkyls or (2) a C3–6 cycloalkyls, optionally partially or fully substituted with C1–7 side chain alkyls or $C_{3-6}$ cycloalkyls and $R^3$ is (1) H or (2) a $C_{1-8}$ n-alkyl, optionally partially or fully substituted with C3–6 cycloalkyls or $C_{1-7}$ side chains or (3) $C_{3-6}$ cycloalkyls, optionally partially or fully substituted with $C_{1-7}$ side chain alkyls or $C_{3-6}$ cycloalkyls.

Preferably when $R_2$ is an n-alkyl group it is a t-butyl or a $C_{4-8}$ n-alkyl group and when $R_2$ is a cycloalkyl group it is a $C_6$ cycloalkyl group.

DETAILED DESCRIPTION OF THE INVENTION

We have further found that in the vast majority of instances, highly and unexpectedly superior antimicrobial activity is supplied by AA's of the above formulae containing t-butyl (tert-butyl) as at least one and preferably two (or even or more) of the $R^2$ and $R^4$ values.

This invention is at least in part based on our further findings that:

1. tert-butyl (t-butyl) substitution at the ortho position of an unsubstituted phenol can enhance its antimicrobial effect by a factor of 10.
2. A second tert-butyl substitution at the 4 (para) position of an ortho tert-butyl substituted phenol can enhance the antimicrobial effect of the resultant by an additional factor of 10.

As described herein other alkyl phenol AA's also provide enhanced antibacterial effectiveness for prevention or reduction of plaque formation.

By way of further example, phenols of the type (1)

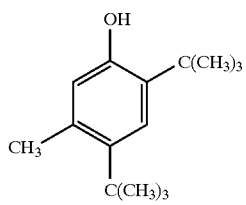

2,4-di-t-butyl-5-methylphenol (2)

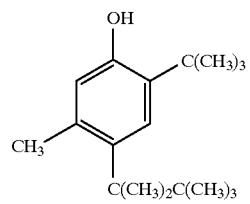

2-t-butyl-4-(1,1,2,2-tetramethylpropyl)-5-methylphenol and (3)–(7)

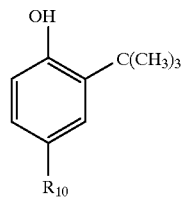

wherein
(3) $R^{10}$=—$C(CH_3)_3$(t-butyl)
(4) $R^{10}$=—$C(CH_3)_2CH_2CH_3$(1,1-dimethylpropyl)
(5) $R^{10}$=—$C(CH_3)_2CH_2CH_2CH_3$(1,1-dimethylbutyl)
(6) $R^{10}$=—$C(CH_3)_2C(CH_3)_3$(1,1,2,2-tetramethylpropyl)
(7) $R^{10}$=—$C(CH_3)_2CH_2C(CH_3)_3$(1,3,3-tetramethylbutyl) 1,1,3,3-tetramethylbutyl)

It will be understood that related compounds active as AA agents can be employed containing indicated variations in values, numbers and/or positions of $R_4$ and $R_2$ and $R_3$, as for example:

2,4-diisohexylphenol
2,4-dicyclopropylphenol
2-cyclohexyl-4-t-butylphenol
2-cyclohexyl-4-n-heptylphenol
2,4-di-t-butyl-5-isopropylphenol
2-t-butyl-4-isopropyl-5-ethylphenol
2-isopropyl-4-t-butyl-5-butylphenol
2-(4'-t-butylcyclohexyl)-4-methyl-5-amylphenol
2-(1,1 -dimethylpropyl)-4-t-butylphenol
2-(1-cyclobutylhexyl)-4-octylphenol
2-isopropyl-5-cyclohexylmethylphenol
2-isopropyl-4-cyclohexylphenol
2-t-octyl-5-cyclohexylmethylphenol
2-cyclohexylmethyl-4-t-butylphenol
2-t-butyl-5-cyclohexylmethylphenol
2-t-butyl-4-n-heptylphenol
2-t-butyl-5-(4-t-butylcyclohexyl)-phenol The improved antimicrobial activities attainable in accordance with this invention generally involve use of branched in preference to straight chains, selective positioning of substituents, increased numbers of substituents and/or the carbon content of alkyl substituents. The improved antimicrobial activities are unexpected, particularly in view of teachings to the contrary in the prior art. For example, C. M. Suter, Chem. Rev. 28 269–299(1941), in discussing phenol coefficients of alkylphenols v. *B. typhosus* and *Staph. aureus*, states (a) "the position of the alkyl group has no effect", and (b) "the o-and p-sec-butyl phenols have phenol coefficients of 28, and the branching of the carbon side chain, as in tert.butylphenol, reduces the effectiveness to about 20" (p. 272), and also (c) "the generalization that the straight-chain primary alkylphenols are more effective than their isomers " (p. 273), "(d) It was concluded that the isobutyl compounds were probably less effective than their n-butyl isomers", and also (e)". As in the alkylphenols, branching of the carbon chain reduces the effectiveness" (p. 275). The microorganisms employed in the above-quoted situations were not those generally encountered in the oral cavity.

Evans et al, J. Periodontol. 48, 156–162 (1977) in an article entitled "In Vitro Antiplaque Effects of Antiseptic Phenols" concludes that whereas "3,5,4'-tribromosalicylanilide was found to be effective against growth and plaque formation of *A. viscosus, A. naeslundii, S. mutans* and *S. sanguis*, Dibromsalicil was found effective against *A. viscosus*. The other phenols (hexylresorcinol, thymol, phenylphenol and zinc phenolsulfonate) did not inhibit in vitro growth or plaque formation".

It will be understood that in the AA compounds employed in the oral compositions of this invention, the $C_{1-7}$ and $C_{1-8}$ side chain and n-alkyls range from methyl to heptyl and octyl and the $C_{3-6}$ cycloalkyls range from cyclopropyl to cyclohexyl. These AA's generally range in molecular weight (M.W.) from about 175 to about 500, preferably about 190 to about 350, more preferably about 210 to about 310. The AA is employed in the oral compositions of the invention in a non-toxic, effective antiplaque amount, typically in a range of about 0.003–5%, preferably about 0.005–3%, more preferably about 0.02–1%. The pH of the oral compositions of this invention may range from about 4.0 to about 9.0.

To increase substantivity and enhance the antibacterial activity of the AA even more, an antibacterial enhancing agent (AEA) may be included in the oral composition. The use of AEA's in combination with water-insoluble noncationic antibacterial compounds is known to the art, as for example U.S. Pat. Nos. 5,188,821 and 5,192,531. An AEA agent is an organic material which contains a delivery-enhancing group and a retention-enhancing group. As employed herein, the delivery-enhancing group refers to one which attaches or substantively, adhesively, cohesively or otherwise bonds the AEA agent (carrying the AA compound) to oral (e.g. tooth and gum) surfaces, thereby "delivering" the compound to such surfaces. The organic retention-enhancing group, generally hydrophobic, attaches or otherwise bonds the AA to the AEA, thereby promoting retention of the AA to the AEA and indirectly on the oral surfaces. The enhanced retention of the AA on the oral surfaces results in an improvement in the retardation of plaque growth on oral surfaces.

Preferably, the AEA is an anionic polymer comprising a chain or backbone containing repeating units each preferably containing at least one carbon atom and preferably at least one directly or indirectly pendent, monovalent delivery-enhancing group and at least one directly or indirectly pendent monovalent retention-enhancing group geminally, vicinally or less preferably otherwise bonded to atoms, preferably carbon, in the chain.

The AEA may be a simple compound, preferably a polymerizable monomer, more preferably a polymer, including for example oligomers, homopolymers, copolymers of two or more monomers, ionomers, block copolymers, graft copolymers, cross-linked polymers and copolymers, and the like, The AEA may be natural or synthetic, and water insoluble or preferably water (saliva) soluble or swellable (hydratable, hydrogel forming) having an (weight) average molecular weight of about 100 to about 5,000,000, preferably about 1,000 to about 1,000,000, more preferably about 25,000 to 500,000.

In the case of the polymeric AEA's, it is desirable, for maximizing delivery and retention of the AA to oral surfaces, that the repeating units in the polymer chain or back-bone containing the acidic delivery enhancing groups constitute at least about 10%, preferably at least about 50%, more preferably at least about 80% up to 95% or 100% by weight of the polymer.

The AEA generally contains at least one delivery-enhancing group, which is preferably acidic such as sulfonic, phosphinic, or more preferably phosphonic or carboxylic, or a salt thereof, e.g. alkali metal or ammonium and at least one organic retention-enhancing group, such typically groups having the formula —$(X)_n$—R wherein X is O, N, S, SO, SO2, P, PO or Si or the like, R is hydrophobic alkyl, alkenyl, acyl, aryl, alkaryl, aralkyl, heterocyclic or their inert-substituted derivatives, and n is zero or 1 or more. The aforesaid "inert-substituted derivatives", are intended to include substituents on R which are generally non-hydrophilic and do not significantly interfere with the desired function of the AEA as enhancing the delivery of the AA to and retention thereof on oral surfaces such as halo, e.g. Cl, Br, I, and carbo and the like. Illustrations of such retention-enhancing groups are tabulated below.

| -n | X | —$(X)_n$R |
|---|---|---|
| 0 | — | methyl, ethyl, propyl, butyl, isobutyl, t-butyl cyclohexyl, allyl, benzyl, phenyl, chlorophenyl, xylyl, pryridyl, furanyl, acetyl, benzoyl, butyryl, terephthaloyl. |
| 1 | O | ethoxy, benzyloxy, thioacetoxy, phenoxy, carboethoxy, carbobenzyloxy. |
|  | N | ethylamino, diethylamino, propylamido, benzylamino, benzoylamido, phenylacetamido. |
|  | S | thiobutyl, thioisobutyl, thioallyl, thiobenzyl, thiophenyl, thiopropionyl, phenylthioacetyl, thiobenzoyl. |
|  | SO | butylsulfoxy, allylsulfoxy, benzylsulfoxy, phenylsulfoxy. |
|  | $SO_2$ | butylsulfonyl, allylsulfonyl, benzylsulfonyl, phenylsulfonyl. |
|  | P | diethylphosphinyl, ethylvinylphosphinyl, ethylallylphosphinyl, ethylbenzylphosphinyl, ethylphenylphosphinyl. |
|  | PO | diethylphosphinoxy, ethylvinylphosphinoxy, methylallylphosphinoxy, methylbenzylphosphinoxy, methylphenylphosphinoxy. |
|  | Si | trimethylsilyl, dimethylbutylsilyl, dimethylbenzylsilyl, dimethylvinylsilyl, dimethylallylsilyl. |

Preferably, the AEA is a natural or synthetic anionic polymeric polycarboxylate having a molecular weight of about 1,000 to about 5,000,000, preferably about 30,000 to about 500,000.

The synthetic anionic polymeric polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl either/maleic anhydride having a molecular weight (M.W.) of about 30,000 to about 1,000,000, most preferably about 30,000 to about 500,000. These copolymers are available, for example, as Gantrez®, e.g. AN 139 (M.W. 500,000), AN 119 (M.W. 250,000); and preferably S-97 Pharmaceutical Grade (M.W. 70,000), of GAF Corporation.

Other polymeric polycarboxylates containing or modified to contain retention enhancing groups operative in the practice of the present invention include the 1:1 copolymers of maleic anhydride with ethyl acrylate, hydroxyethyl methacrylate, N-vinyl-2-pyrollidone, or ethylene, the latter being available, for example, as Monsanto EMA® No: 1103, M.W. 10,000 and Grade 61, and 1:1 copolymers of acrylic acid with methyl or hydroxyethyl methacrylate, methyl or ethyl acrylate, isobutyl methacrylate, isobutyl vinyl ether or N-vinyl-2-pyrrolidone.

Additional operative polymeric polycarboxylates containing or modified to contain retention enhancing groups include copolymers of maleic anhydride with styrene, isobutylene or ethyl vinyl either, polyacrylic, polyitaconic and polymaleic acids, and sulfonacrylic oligomers of M.W. as low as 1,000 available as Uniroyal® ND-2.

Also suitable for use in the practice of the present invention are polymerized olefinically or ethylenically unsaturated carboxylic acids containing an activated carbon-to-carbon olefinic double bond which readily functions on polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, betastyrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

Also useful in the practice of the present invention are so-called carboxyvinyl polymers. They are commercially available, for example, under the trademarks Carbopol® 934, 940 and 941 of B. F. Goodrich, these products consisting of a colloidally water-soluble polymer of polyacrylic acid crosslinked with from about 0.75% to about 2.0% of polyallyl sucrose or polyallyl pentaerythritol as a cross linking agent, often with M.W.'s up to 4–5 million or more.

Illustrative of AEA's containing phosphinic acid and/or sulfonic acid delivery enhancing groups, are polymers and copolymers containing units or moieties derived from the polymerization of vinyl or allyl phosphinic and/or sulfonic acids substituted as needed on the 1 or 2 or 3 carbon atom by an organic retention-enhancing group, for example having the formula —(X)$_n$—R defined above. Mixtures of these monomers may be employed, and copolymers thereof with one or more inert polymerizable ethylenically unsaturated monomers such as those described above with respect to the operative synthetic anionic polymeric polycarboxylates.

As an example of a polymer containing repeating units in which one or more phosphonic acid delivery-enhancing groups are bonded to one or more carbon atoms in the polymer chain is poly(vinyl phosphonic acid) containing units of the formula:

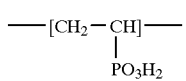

A.

which may be an AEA even though it does not contain a retention-enhancing group. A group of the latter type would however be present in poly (1-phosphonopropene) with units of the formula:

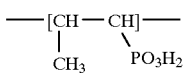

B.

A preferred phosphonic acid-containing polymer for use herein is poly (beta styrene phosphonic acid) containing units of the formula:

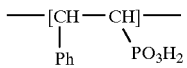

C.

wherein Ph is phenyl, the phosphonic delivery-enhancing group and the phenyl retention-enhancing group being bonded on vicinal carbon atoms in the chain, or a copolymer of beta styrene phosphonic acid with vinyl phosphonyl chloride having the units of formula C alternating or in random association with units of formula I above, or poly (alpha styrene phosphonic acid) containing units of the formula:

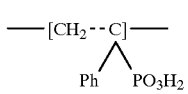

D.

in which the delivery—and retention-enhancing groups are terminally bonded to the chain.

These styrene phosphonic acid polymers and their copolymers with other inert ethylenically unsaturated monomers generally have molecular weights in the range of about 2,000 to about 30,000, preferably about 2,500 to about 10,000.

Other phosphonic-containing polymers include, for example, phosphonated ethylene having units of the formula:

$$—[CH_2)_{14}CHPO_3H_2]_n—$$ (E.)

where n may for example be an integer or have a value giving the polymer a molecular weight of for example about 3,000; and sodium poly (butene-4,4-diphosphonate) having units of the formula:

and poly(allyl bis (phosphonoethyl) amine) having units of the formula:

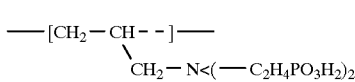

F.

Other phosphonated polymers, for example poly (allyl phosphono acetate), phosphonated polymethacrylate, etc. and the geminal diphosphonate polymers disclosed in EP Publication 0321233 are also useful in the practice of the present invention preferably provided that they contain or are modified to contain the above-defined organic retention-enhancing groups.

Polysiloxanes containing or modified to contain pendant delivery-enhancing groups and retention enhancing groups such as liquid silicone oils such as diphenyl or di($C_1$–$C_4$) alkyl polysiloxanes and particularly dimethyl-polysiloxane, may also be employed in the practice of the present invention.

Also effective herein are ionomers containing or modified to contain delivery-and-retention-enhancing groups. Ionomers are described on pages 546–573 of the Kirk Othmer Encyclopedia of Chemical Technology, third edition, Supplement Volume, John Wiley & Sons, Inc. copyright 1984, which description is incorporated herein by reference. Also effective herein, provided they contain or are modified to contain retention-enhancing groups, are polyesters, polyurethanes and synthetic and natural polyamides including proteins and proteinaceous materials such as collagen, poly (arginine) and other polymerized amino acids.

The AEA, when employed, is incorporated in the compositions of the present invention in weight amounts of about 0.05 to about 5%, preferably about 0.1 to about 3%.

Linear molecularly dehydrated polyphosphate salts can be optionally employed herein as anticalculus agents. They are well known, being generally employed in the form of their wholly or partially neutralized water soluble alkali metal (e.g. potassium or preferably sodium) or ammonium salts, and any mixtures thereof. Representative examples include sodium hexametaphosphate, sodium tripolyphosphate, monosodium triacid-, disodium diacid-, trisodium monoacid-, and tetrasodium-pyrophosphates, the corresponding potassium salts and the like. In the present invention, they can be employed in the oral compositions in approximate weight amounts of about 0.1 to 3%, typically 1 to 2.5%, more typically 1.5 to 2%, especially 1It about 2%.

Particularly desirable anticalculus agents are tetraalkali metal pyrophosphates such as tetrasodium and tetrapotassium pyrophosphates, and mixtures thereof.

In the oral compositions, when both AEA and polyphosphate are present, the weight ratio of the AEA to polyphosphate ions is typically about 1.6:1 to about 2.7:1, preferably about 1.7:1 to about 2.3:1, more preferably about 1.9:1 to abut 2:1.

Fluoride ions may desirably also be included in the oral compositions of this invention, being in effect multifunctional in providing an anticaries effect or tooth-hardening effect and, in optional conjunction with the AEA, in inhibiting the salivary enzymatic hydrolysis of the polyphosphate anticalculus agent, when employed.

An amount of a source of fluoride ions, or fluorine-providing component, may be included to provide or supply about 25 ppm to 5,000 ppm of fluoride ions.

These compounds may be slightly soluble in water or may be fully water-soluble. They are characterized by their ability to release fluoride ions in water and by substantial freedom from undesired reaction with other compounds of the oral composition. Among these materials are inorganic fluoride salts, such as soluble alkali metal, alkaline earth metal salts, for example, sodium fluoride, potassium fluoride, ammonium fluoride, calcium fluoride, a cuprous fluoride, zinc fluoride, barium fluoride, sodium monofluorophosphate, aluminum mono-and di-fluorophosphate and sodium calcium fluorophosphate. Alkali metal and tin fluorides, such as sodium and stannous fluorides, sodium monofluorophosphate (MFP) and mixtures thereof, are preferred.

The amount of fluorine-providing compound is dependent to some extent upon the type of compound, its solubility, and the type of oral composition, but it must be a non-toxic amount, generally about 0.0005 to about 3.0% in the preparation. Any suitable minimum amount of such compound may be used, but it is preferable to employ sufficient compound to release about 300 to 2,000 ppm, more preferably about 800 to about 1,500 ppm of fluoride ion.

Typically, in the cases of alkali metal fluorides, this component is present in an amount up to about 2% by weight, based on the weight of the composition, and preferably in the amount of about 0.05% to 1%, more typically about 0.2 to 0.35% for sodium fluoride. In the case of sodium monofluorophosphate, the compound may be present in an amount of about 0.1–3%, more typically about 0.76% by weight.

The oral composition of the present invention may be a solution of ingredients such as a mouthrinse or it maybe a semi-solid such as a toothpaste or gel dentifrice which may contain 0 to 75% of polishing agent, or chewing gum or solid lozenge or the like.

Oral gel preparations contain a siliceous polishing material including crystalline silica having particle sizes of up to about 5 microns, silica gel, colloidal silica or complex amorphous alkali metal aluminosilicate.

When visually clear or opacified gels are employed, a polishing agent of colloidal silica, such as those sold under the trademark Sylox® as Silox 15, or under the trademark Syloid® as Syloid 72 and Syloid 74, or under the trademark Santocel® as Santocel 100, or under the trademark Zeodent® as Zeodent 113 or alkali metal aluminosilicate complexes (that is, silica containing alumina combined in its matrix) are particularly useful, since they are consistent with gel-like texture and have refractive indices close to the refractive indices of gelling agent-liquid (including water and/or humectant) systems commonly used in dentifrices.

In the aspect of this invention wherein the oral composition is a gel or paste, an orally acceptable vehicle, including a water-phase with humectant which is preferably glycerine or sorbitol or an alkylene glycol such as polyethylene glycol or propylene glycol is present, wherein water is present typically in an amount of about 15–40% by weight and glycerine, sorbitol and/or the alkylene glycol (preferably propylene glycol) typically total about 20–75% by weight of the oral composition, more typically about 25–60%.

When the oral composition is substantially semi-solid or pasty in character, such as a toothpaste (dental cream), the vehicle of the dentifrice contains a dentally acceptable polishing material such as sodium bicarbonate or water insoluble polishing material such as sodium metaphosphate, potassium metaphosphate, tricalcium phosphate, dihydrated dicalcium phosphate, anhydrous dicalcium phosphate, calcium pyrophosphate, calcium carbonate, aluminum silicate, hydrated alumina, silica, bentonite, and mixtures thereof with each other or with minor amounts of hard polishing materials such as calcined alumina and zirconium silicate. Preferred polishing materials include silica, insoluble sodium metaphosphate, dicalcium phosphate, calcium pyrophosphate and hydrated alumina, as well as sodium bicarbonate.

The polishing material is generally present in the gel, cream or paste compositions in weight concentrations of about 10% to about 75% by weight, preferably about 10% to about 30% in a gel and about 25% to about 75% in a cream or paste.

Toothpastes or dental cream dentifrices as well as gel dentifrices typically contain a natural or synthetic thickener or gelling agent in proportions of about 0.1 to about 10%, preferably about 0.5 to about 5%.

Suitable thickeners or gelling agents include Irish moss, iota-carrageenan, kappa-carrageenan, gum tragacanth, starch, polyvinylpyrrolidone, hydroxyethyl propyl cellulose, hydroxybutyl methyl cellulose, hydroxypropyl methyl cellulose, hydroxyethyl cellulose and sodium carboxymethyl cellulose.

In the aspect of the present invention wherein the oral composition is substantially liquid in character such as a mouthwash or rinse, the vehicle is typically a water-alcohol mixture. Generally, the weight ratio of water to alcohol is in the range of from about 3:1 to 10:1 and preferably about 4:1 to about 6:1. The alcohol is a non-toxic alcohol such as ethanol or isopropanol. A humectant such as glycerine, sorbitol or an alkylene glycol such as polyethylene glycol or preferably propylene glycol may be present in amount of about 10–30% by weight. Mouthrinses typically contain about 50–85% of water, about 0 to 20% by weight of a non-toxic alcohol and about 10–40% by weight of the humectant.

Organic surface-active agents are used in the compositions of the present invention to achieve increased prophylactic action, assist in achieving thorough and complete dispersion of the AA throughout the oral cavity, and render the instant compositions more cosmetically acceptable. The organic surface-active material is preferably anionic, non-ionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals and alkoyl taurines, and the like. Examples of the last mentioned amides and taurates are N-lauroyl sarcosine, and the sodium, potassium and ethanolamine salts of N-lauroyl, N-myristoyl, or N-palmitoyl sarcosine which should be substantially free from soap or similar higher fatty acid material as well as N-methyl-N-cocoyl (or oleoyl or palmitoyl) taurines. The use of these sarcosinate compounds in the oral compositions of the present invention is often advantageous since these materials exhibit a prolonged and marked effect in the inhibition of acid formation in the oral cavity due to carbohydrate breakdown in addition to exerting some reduction in the solubility of tooth enamel in acid solutions.

Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic® materials).

Examples of polyoxamers useful in the practice of the present invention include block copolymers of polyoxyethylene and polyoxypropylene having an average molecular weight from about 3000 to 5000 and a preferred average molecular weight from about 3500 to about 4000 and containing about 10–80% hydrophilic polyoxyethylene groups, by weight, of the block copolymer. A preferred polyoxamer useful in the practice of the present invention is Pluronic F127 (trademark) a block copolymer of polyoxyethylene and polyoxypropylene having a molecular weight of about 4000.

Any suitable flavoring or sweetening material may also be employed. Examples of suitable flavoring constituents are flavoring oils, e.g. oil of spearmint, peppermint, wintergreen, sassafras, clove, sage, eucalyptus, cinnamon, lemon, and orange, and methyl salicylate. Suitable sweetening agents include sucrose, lactose, maltose, xylitol, sodium cyclamate, perillartine, aspartyl phenyl alanine methyl ester, saccharine and the like. Suitably, flavor and sweetening agents may each or together comprise from about 0.1% to 5% or more of the preparation.

Agents used to diminish teeth sensitivity such as strontium chloride, potassium nitrate and potassium citrate can also be included in the oral compositions of the present invention at concentrations of about 0.1 about 10% by weight.

Various other materials may be incorporated in the oral compositions of this invention including whitening agents such as urea peroxide and hydrogen peroxide, preservatives, such as sodium benzoate, chlorophyll compounds and/or ammoniated material such as urea, diammonium phosphate, and mixtures thereof. These adjuvants, when present, are incorporated in the compositions in amounts which do not substantially adversely affect the properties and characteristics desired.

The oral compositions of the present invention may be prepared by suitably mixing the ingredients. For instance, in the preparation of a mouthrinse, the AA is dispersed in a mixture of ingredients, e.g. alcohol, humectants, surfactants, and ABA and salts such as sodium fluoride and potassium phosphate, and flavor are then added and mixed. The ingredients are then mixed under vacuum for about 15–30 minutes. The resulting rinse is then packaged. Dentifrices are prepared similarly, the additional thickener and polishing agents being included in the last or penultimate step.

In the preferred practice of this invention an oral composition according to this invention such as a dentifrice is preferably applied as by brushing regularly to dental enamel, such as every second or third day or preferably from 1 to 3 times daily, at a pH of about 4.5 to 10, generally about 5.5 to 9, preferably about 6 to 8, for at least 2 weeks up to 8 weeks or more up to lifetime. The dentifrice is typically removed by rinsing with water after each application. Mouthrinses are rinsed or gargled in similar systematic manner.

The compositions of this is invention can be incorporated in lozenges, or in chewing gum or other products, e.g. by stirring into a warm gum base or coating the outer surface of a gum base, illustrative of which may be mentioned jelutone, rubber latex, vinylite resins, etc., desirably with conventional plasticizers or softeners, sugar or other sweeteners or carbohydrates such as glucose, sorbitol and the like.

The vehicle or carrier in a tablet or lozenge is a non-cariogenic solid water-soluble polyhydric alcohol (polyol) such as mannitol, xylitol, sorbitol, malitol, a hydrogenated starch hydrolysate, Lycasin, hydrogenated glucose, hydrogenated disaccharides or hydrogenated polysaccharides, in an amount of about 90 to 98% by weight of the total composition. Solid salts such as sodium bicarbonate, sodium chloride, potassium bicarbonate or potassium chloride may totally or partially replace the polyol carrier.

Tableting lubricants, in minor amounts of about 0.1 to 5% by weight, may be incorporated into the tablet or lozenge formulation to facilitate the preparation of both the tablets and lozenges. Suitable lubricants include vegetable oils such as coconut oil, magnesium stearate, aluminum stearate, talc, starch and Carbowax®.

Lozenge formulations contain about 2% gum as a barrier agent to provide a shiny surface as opposed to a tablet which has a smooth finish. Suitable non-cariogenic gums include kappa carrageenan, carboxymethyl cellulose, hydroxyethyl cellulose, Gantrez®, and the like.

The lozenge or tablet may optionally be coated with a coating material such as waxes, shellac, carboxymethyl cellulose, polyethylene/maleic anhydride copolymer or kappa-carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet and lozenge composition of this invention affords a relatively longer time period of contact of the teeth in the oral cavity with the active ingredients.

In the Tables below following illustrative Example 5, AA's are listed. These AA's are indicated to be 10 to 100 or more times more active than thymol. 100 times the activity of thymol would be comparable to triclosan in antiplaque activity.

The AA's are made synthetically by conventional alkylation methods such as Friedel-Crafts alkylation.

The SIKT (Short Interval Kill Test) test referred to in the examples is used to assess the ability of actives to kill in a short period of time (e.g. 2 minutes), simulating antiplaque mouthrinse conditions. In this test, which is described in U.S. Pat. No. 5,275,805, column 11, lines 10–28, which description is herewith incorporated herein, control and test samples are mixed with pre-determined innoculums of $S.$ $sanguis$, $S.$ $mutans$ and $S.$ $viscosus$ ($10^6$–$10^7$ colony forming unit (cfu/nml.)) for 2 minute contact times, the systems then neutralized to inhibit further antibacterial activity, and the surviving bacteria enumerated using plate count methodology. The reduction in cfu counts compared to the water control is the basis for expressing the antibacterial activity of the test agents, i.e. as % killing in comparison to the appropriate placebo or control.

The MIC Minimum Inhibitory Concentration) test referred to in the examples measures the minimum concentration in ppm or mM of the AA at which the growth of the bacteria (same 3 plaque involved species as employed in the SIKT tests) is completely inhibited by the AA. The smaller the MIC, the greater the antibacterial activity of the AA being tested. This MIC test is also described in U.S. Pat. No. 5,275,805 at column 11, lines 54–68, which description is herewith incorporated herein.

The following examples are further illustrative of the nature of the present invention, but it is understood that the invention is not limited thereto. All amounts and proportions referred to herein and in the appended claims are by weight unless otherwise indicated.

EXAMPLES 1 & 2

| | Liquid Dentifrice Composition | | |
|---|---|---|---|
| Ingredients | Placebo (g.) | Example 1 (g.) | Example 2 (g.) |
| Glycerol (99.7% stock) | 20.000 | 20.000 | 20.000 |
| Sorbitol (70% stock) | 20.000 | 20.000 | 20.000 |
| Propylene glycol | 0.500 | 0.500 | 0.500 |
| Sodium lauryl sulfate | 1.500 | 1.500 | 1.500 |
| Gantarez (13.2% stock) S97 | 15.150 | 15.150 | 15.150 |
| Triclosan | | | 0.300 |

-continued

| | Liquid Dentifrice Composition | | |
|---|---|---|---|
| Ingredients | Placebo (g.) | Example 1 (g.) | Example 2 (g.) |
| 2,4-di-t-butyl phenol | | 0.300 | |
| Sodium fluoride | 0.243 | 0.243 | 0.243 |
| Water | 18.300 | 18.000 | 18.000 |
| Flavor | 1.000 | 1.000 | 1.000 |
| pH 7.00 | | | |

MIC Liquid Dentifrice Test Results

| | Bacterial species (MIC in ppm) | | |
|---|---|---|---|
| | $A.$ $viscosus$ | $S.$ $sanguis$ | $S.$ $mutans$ |
| Placebo | 7.80 | 7.80 | 3.90 |
| Triclosan (Example 2) | 3.90 | 3.90 | 3.90 |
| 2,4-di-t-butylphenol (Example 1) | 7.80 | 3.90 | 3.90 |

In this MIC test the Example 3 formulation of this invention exhibits antibacterial activity equal to the triclosan Example 4 formulation v. $S.$ $sangius$ and $S.$ $mutans$ and double that of the placebo v. $S.$ $sanguis.$

SIKT Liquid Dentifrice Results

| | SIKT (% killing) |
|---|---|
| Triclosan (Example 2) | 92 |
| 2,4-di-t-butylphenol (Example 1) | 80 |

In the control (water), the amount of bacteria present is $10^4$ cells/ml. In comparison 10–15 colony forming units (CFU's) are considered to be 100% kill. These SIKT tests show the antibacterial activity of the Example 1 formulation of this invention to achieve 100% kill and to be substantially like the triclosan Example 2 formulation.

EXAMPLE 3

Mouthwash formulation containing 2-cyclohexylmethyl-4-t-butylphenol

| Ingredients | % |
|---|---|
| Sorbitol (70%) | 10.00 |
| Glycerin (99.7%) | 10.00 |
| Ethanol (95%) | 15.00 |
| Propylene glycol | 15.00 |
| Sodium lauryl sulfate | 0.50 |
| Tauranol (97%)* | 0.25 |
| Pluronic F127** | 0.25 |
| Mint flavor | 0.10 |
| 2-cyclohexylmethyl-4-t-butylphenol | 0.03 |
| Water | 48.87 |
| Total | 100.00 |

*Sodium methyl cocoyl taurate, trademark.
**Block copolymer polyoxypropylene/polyoxyethylene, M.W. 4000, trademark.

EXAMPLE 4

Toothpaste formulation containing 2-t-octyl-5-cyclohexylmethylphenol

| Ingredients | % |
| --- | --- |
| 2-t-octyl-5-cyclohexylmethylphenol | 0.30 |
| Sodium monofluorophosphate | 0.19 |
| Propylene glycol | 30.00 |
| Glycerin (99.7%) | 10.00 |
| Zeodent 115* | 20.00 |
| Sorbitol (70%) | 25.00 |
| Water | 7.61 |
| Sylodent 15** | 2.00 |
| Sodium lauryl sulfate | 0.50 |
| Pluronic F127 | 0.50 |
| Tauranol (97%) | 0.50 |
| Flavor | 1.00 |
| $K_2HPO_4$ | 0.50 |
| Sodium carboxymethyl cellulose | 0.80 |
| Titanium dioxide | 0.50 |
| Iota-carrageenan*** | 0.30 |
| Sodium saccharin | 0.30 |
| Total | 100.00 |

*Silica polishing agent, trademark.
**Silica thickener, trademark.
***Thickener, stabilizer.

The above formulation can be modified by replacing some or all Zeodent 115 silica polishing agent and Sylodent 15 silica thickener with sodium bicarbonate, insoluble sodium metaphosphate, dicalcium phosphate, calcium pyrophosphate, hydrated alumina and mixtures thereof.

In the following Example 5 the tests are carried out in neat solutions of the AA active agent in 98.5% ethanol (EtOH) which, at the test concentrations, does not show any antibacterial properties.

EXAMPLE 5

Minimum Inhibitory Concentration (MIC) Results

| | Bacterial species (MIC in ppm) | | |
| --- | --- | --- | --- |
| | A. viscosus | S. sanguis | S. mutans |
| 2,4-di-t-butylphenol | 1.95 | 1.95 | 0.98 |
| Thymol | 15.60 | 15.60 | 31.25 |
| Triclosan | 0.50 | 0.98 | 1.95 |

In this test, the 2,4-di-t-butyl phenol is found to be many times superior to thymol, significantly superior to triclosan against S. mutans and somewhat less active than triclosan I: against A. viscosus and S. sanguis.

The following Tables list AA's with activities compared to thymol and triclosan. Predicted MIC's in mM are indicated as well as found values for several of them.

Predicted values are based on our above-referred to findings and other criteria including consideration of types, sizes, numbers and positions of substituents, their structure (straight, branched, cyclic alkyl), etc. The Tables show that the AA's have substantially lower predicted and found MIC's than thymol. The values predicted can vary from earlier predictions for the same compound as experience is gained with modeling predictions. The values found can vary from test to test. Comparisons based on predictions and found values are relevant for data predicted and found contemporaneously. The data in each of Tables 1 and 2 were obtained contemporaneously for each Table.

TABLE I

| | MIC (mM) v A. viscosus | |
| --- | --- | --- |
| Phenol | Predicted | Found |
| Thymol | 1.7 | 2.0 |
| Triclosan | — | 0.02 |
| 2,4-di-t-butyl phenol | 0.19 | 0.20 |
| 2,4-di-t-butyl-5-methyl phenol | 0.17 | |
| 2-t-butyl-4-(1,1-dimethylpropyl) phenol | 0.099 | |
| 2-t-butyl-4-(1,1-dimethylbutyl) phenol | 0.098 | |
| 2-t-butyl-4-(1,1,2,2-tetramethylpropyl) phenol | 0.11 | |
| 2-t-butyl-4-(1,1,2,2-tetramethylpropyl)-5-methyl phenol | 0.10 | |

TABLE II

| | MIC (mM) v A. viscosus | |
| --- | --- | --- |
| Phenol | Predicted | Found |
| Triclosan | — | 0.010 |
| Thymol | 1.77 | 2.00 |
| 2-t-butyl-5-cyclohexylmethylphenol | 0.006 | 0.004 |
| 2-t-butyl-4-n-heptylphenol | 0.011 | 0.0086 |
| 2-isopropyl-5-cyclohexylmethylphenol | 0.038 | |
| 2-isopropyl-4-cyclohexylphenol | 0.105 | |
| 2-t-octyl-5-cylohexylmethylphenol | 0.001 | 0.0017 |
| 2-cyclohexylmethyl-4-t-butylphenol | 0.055 | |
| 2-cyclohexyl-4-n-heptylphenol | 0.0035 | |

This invention has been disclosed with respect to preferred embodiments thereof and it will be understood that variations and modifications obvious to those skilled in the art are intended to be included within the purview of this application and the scope of the appended claims.

We claim:

1. An oral composition comprising an orally acceptable vehicle and an effective antiplaque amount of at least one substantially water insoluble noncationic antibacterial agent (AA) of the formula:

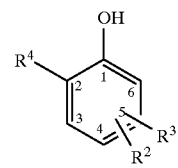

wherein $R^2$ and $R^3$ are interchangeably substituted in the 4 and 5 positions;

wherein $R^4$ is defined below, wherein:

(a) when $R^4$ is $C_1$ n-alkyl, it is partially or fully substituted with $C_{3-6}$ cycloalkyl, which are optionally partially or fully substituted with C3–6 cycloalkyls or $C_{1-7}$ side chains alkyls and $R^2$ is (1) a $C_{1-8}$ n-alkyl, partially or fully substituted with C3–6 cycloalkyls or (2) a $C_{3-6}$ cycloalkyls, optionally partially or fully substituted with C1–7 side chain alkyls or $C_{3-6}$ cycloalkyls and $R^3$ is (1) H or (2) a $C_{1-8}$ n-alkyl, partially or fully substituted with C3–6 cycloalkyls or (3) a $C_{3-6}$ cycloalkyl optionally partially or fully substituted with $C_{1-7}$ side chain alkyls or $C_{3-6}$ cycloalkyls;

(b) when $R^4$ is $C_2$ n-alkyl it is partially or fully substituted with $C_{3-6}$ cycloalkyls which are optionally partially or fully substituted with $C_{1-7}$ side chain alkyls or $C_{3-6}$ cycloalkyls and R² is (1) a C₄₋₈ n-alkyl, partially or fully substituted with C₃₋₆ cycloalkyls or (2) a C₃₋₆ cycloalkyl, optionally partially or fully substituted with C1–7 side chain alkyls or C₃₋₆ cycloalkyls and R³ is (1) H or (2) a C₁₋₈ n-alkyl, partially or fully substituted with C₃₋₆ cycloalkyl or (3) a C₃₋₆ cycloalkyl, optionally partially or fully substituted with C₁₋₇ side chain alkyls or C₃₋₆ cycloalkyls;

(c) when R⁴ is t-butyl it is optionally partially or fully substituted with C₃₋₆ cycloalkyls which are optionally partially or fully substituted with C₁₋₇ side chain alkyls or C₃₋₆ cycloalkyls and R² is (1) a C₁₋₈ n-alkyl, partially or fully substituted with C₃₋₆ cycloalkyls or (2) a C₃₋₆ cycloalkyl, optionally partially or fully substituted with C1–7 side chain alkyls or C₃₋₆ cycloalkyls and R³ is (1) H or (2) a C₁₋₈ n-alkyl, partially or fully substituted with C3–6 cycloalkyls or (3) C₃₋₆ cycloalkyl, optionally partially or fully substituted with C₁₋₇ side chain alkyls or C₃₋₆ cycloalkyls;

(d) when R⁴ is C₃₋₈ n-alkyl it is partially or fully substituted with C₁₋₇ side chain alkyls and R² is (1) a C₂₋₈ n-alkyl, partially or fully substituted with C₃₋₆ cycloalkyls or (2) a C₃₋₆ cycloalkyl; optionally partially or fully substituted with C1–7 side chains or C₃₋₆ cycloalkyls and R³ is (1) H or (2) a C₂₋₈ n-alkyl, partially or fully substituted with C₃₋₆ cycloalkyls or (3) a C₃₋₆ cycloalkyl, optionally partially or fully substituted with C₁₋₇ side chain alkyls or C₃₋₆ cycloalkyls and (e) when R⁴ is C₃₋₆ cycloalkyl it is optionally partially or fully substituted with C₁₋₇ side chain alkyls or C₃₋₆ cycloalkyls and R² is (1) a C₄₋₈ n-alkyl, partially or fully substituted with C₃₋₆ cycloalkyls or C₁₋₇ side chain alkyls or (2) a C3–6 cycloalkyls, optionally partially or fully substituted with C1–7 side chain alkyls or C₃₋₆ cycloalkyls and R³ is (1) H or (2) C₃₋₆ cycloalkyls, optionally partially or fully substituted with C₁₋₇ side chain alkyls or C₃₋₆ cycloalkyls.

2. A composition according to claim 1 wherein R⁴ is t-butyl.

3. An oral composition comprising an orally acceptable vehicle and an effective antiplague amount of a substantially water insoluble noncationic antibacterial agent (AA) selected from the group consisting of 2-t-butyl-4-(1,1-dimethylpropyl)-phenol, 2-t-butyl-4-(1,1-dimethylbutyl)-phenol, 2-t-butyl-4-(1,1,2,2-tetramethylpropyl)-phenol, and 2-t-butyl-4-(1,1,2,2-tetramethylpropyl)-5-methylphenol.

4. An oral composition comprising an orally acceptable vehicle and an effective antiplague amount of a substantially water insoluble noncationic antibacterial agent (AA) selected from the group consisting of 2-t-butyl-5-cyclohexylmethylphenol and 2-t-butyl-4-n-heptylphenol.

5. An oral composition comprising an orally acceptable vehicle and an effective antiplaque amount of 2-t-octal-5-cyclohexylmethylphenol.

6. An oral composition comprising an orally acceptable vehicle and an effective antiplaque amount of 2-cyclohexylmethyl4-t-butylphenol.

7. A composition according to claim 1 wherein R⁴ in the AA is said C₃₋₆ cycloalkyl.

8. A composition according to claim 7 wherein said AA is 2-cyclohexyl-4-n-heptylphenol.

9. A composition according to claim 1 further containing about 0.05–5% of antibacterial-enhancing agent (AEA).

10. A composition according to claim 9 wherein said AEA has an average molecular weight (M.W.) of about 100 to about 5,000,000.

11. A composition according to claim 10 wherein said AEA contains at least one acidic delivery-enhancing group and at least one organic retention-enhancing group.

12. A composition according to claim 11 wherein said delivery-enhancing group comprises carboxylic, phosphonic, phosphinic and/or sulfonic acid groups and salts and any mixtures thereof, and said organic retention-enhancing group has the formula —(X)ₙ—R wherein X is O, N, S, SO, SO₂, P, PO or Si, R is hydrophobic alkyl, alkylene, acyl, aryl, alkaryl, aralkyl, heterocyclic, or their inert-substituted derivatives, and n is 1 or zero.

13. A composition according to claim 12 wherein said AEA is an anionic polymer containing a plurality of said delivery-enhancing and retention-enhancing groups.

14. A composition according to claim 13 wherein said delivery-enhancing group comprises carboxylic or salt thereof.

15. A composition according to claim 14 wherein said AEA is a copolymer of maleic acid or anhydride with another ethylenically unsaturated polymerizable monomer.

16. A composition according to claim 15 wherein said other monomer is methyl vinyl either in a 4:1 to 1:4 molar ratio with the maleic acid or anhydride, and said copolymer has an average M.W. of about 70,000 to 250,000 and comprises about 0.05–3% of the composition.

17. A composition according to claim 13 wherein said delivery-enhancing group comprises phosphonic or salt thereof.

18. A composition according to claim 17 wherein said AEA comprises poly (beta-styrenephosphonic acid) or poly (alpha-styrenephosphonic acid) or a copolymer of either styrenephosphonic acid with another ethylenically unsaturated monomer.

19. A composition according to claim 1 further containing an effective anticalculus amount of at least one linear molecularly dehydrated polyphosphate anticalculus agent.

20. A composition according to claim 19 containing about 0.1 to 3% of said polyphosphate and the weight ratio of said AEA to polyphosphate ion ranges from about 1.6:1 to about 2.7:1.

21. A composition according to claim 18 wherein said polyphosphate comprises tetrasodium or tetrapotassium pyrophosphate or a mixture thereof.

22. A composition according to claim 9 further containing an effective anticalculus amount of at least one linear molecularly dehydrated polyphosphate anticalculus agent.

23. A composition according to claim 12 further containing an effective anticalculus amount of at least one linear molecularly dehydrated polyphosphate anticalculus agent.

24. A composition according to claim 1 further containing about 25–5,000 ppm of fluoride ions.

25. A composition according to claim 12 further containing about 25–5,000 ppm of fluoride ions.

26. A composition according to claim 22 further containing about 25–5,000 ppm of fluoride ions.

27. A composition according to claim 1 wherein the AA has a molecular weight of about 175 to about 500.

28. A composition according to claim 1 wherein the AA has a molecular weight of about 210 to about 310.

29. A composition according to claim 1 wherein said composition contains about 10% to about 75% by weight of a dentally acceptable polishing agent.

30. A composition according to claim 29 wherein said polishing agent is silica.

31. A method for inhibiting dental plaque comprising applying to the teeth a plaque-inhibiting amount of an oral composition as defined in any one of claims 1–2, 3–4, 5, 6–8, 9–30.

* * * * *

UNITED STATES PATENT AND TRADEMARK OFFICE
CERTIFICATE OF CORRECTION

PATENT NO. : 5,912,274
DATED : June 15, 1999
INVENTOR(S) : Stringer et al

It is certified that error appears in the above-indentified patent and that said Letters Patent is hereby corrected as shown below:

On the cover page of the patent at item [75] Inventors: should read, "Orum, D. Stringer; John C. Brahms; Malathy Subramanian; Ernest E. Kelly and Stuart Shapiro, Kilchberg, Switzerland Signed and Sealed this Sixteenth Day of November, 1999

Attest:

Q. TODD DICKINSON

*Attesting Officer*  *Acting Commissioner of Patents and Trademarks*